US010207150B2

(12) United States Patent
Noorzai et al.

(10) Patent No.: US 10,207,150 B2
(45) Date of Patent: Feb. 19, 2019

(54) COMBINATION THERAPEUTIC AND EXERCISE SYSTEM

(71) Applicants: Mustafa Noorzai, Moorpark, CA (US); Jack W. Broudy, Carlsbad, CA (US); Omar Noorzai, Camarillo, CA (US); George J. Huang, Rancho Cucamonga, CA (US)

(72) Inventors: Mustafa Noorzai, Moorpark, CA (US); Jack W. Broudy, Carlsbad, CA (US); Omar Noorzai, Camarillo, CA (US); George J. Huang, Rancho Cucamonga, CA (US)

(73) Assignee: INFINITY KEYBOARD, INC., Moorpark, CA (US)

( * ) Notice: Subject to any disclaimer, the term of this patent is extended or adjusted under 35 U.S.C. 154(b) by 658 days.

(21) Appl. No.: 14/858,656

(22) Filed: Sep. 18, 2015

(65) Prior Publication Data
US 2016/0220868 A1    Aug. 4, 2016

Related U.S. Application Data

(60) Provisional application No. 62/111,110, filed on Feb. 3, 2015.

(51) Int. Cl.
*A63B 26/00* (2006.01)
*A61F 7/00* (2006.01)
(Continued)

(52) U.S. Cl.
CPC .............. *A63B 26/003* (2013.01); *A61F 7/00* (2013.01); *A63B 22/14* (2013.01); *A63B 22/16* (2013.01);
(Continued)

(58) Field of Classification Search
CPC .............. A61F 7/00; A61F 2007/0045; A61H 2201/168; A61H 2201/0207;
(Continued)

(56) References Cited

U.S. PATENT DOCUMENTS 3,612,519 A    10/1971  Larson
4,220,329 A *  9/1980  Agyagos ............... A63B 22/14
                                                        482/147
(Continued)

FOREIGN PATENT DOCUMENTS

GB           2375492         11/2002

OTHER PUBLICATIONS

Young, Lee W.; International Search Report and Written Opinion; PCT/US 16/15826; dated Apr. 22, 2016; 9 pages.

*Primary Examiner* — Quang D Thanh
(74) *Attorney, Agent, or Firm* — Stetina Brunda Garred and Brucker

(57) ABSTRACT

An active exercise and therapeutic system for promoting physical motion, balance and coordination and importantly a variety of therapeutic modalities to a user's foot or feet. The system includes a training apparatus having a stationary base member operatively interconnected with first and second rotating platforms mounted thereon. The first and second rotating platforms are adapted to receive, respectively, the foot of an individual to stand thereon such that each foot can rotate independently about a separate axis. Stationary base member with rotating platforms mounted thereon can further be positioned upon a specialized mount operative to impart a further range of motion or specific orientation. In further embodiments, the rotating platforms may be provided with a variety of functional modalities, such as calorie counting, distance travelled, and the like, or a therapeutic
(Continued)

modality, such as heat, cold or pressure sensation to impart a therapeutic effect to the user's feet.

10 Claims, 6 Drawing Sheets

(51) Int. Cl.
| | |
|---|---|
| *A63B 22/16* | (2006.01) |
| *A63B 22/14* | (2006.01) |
| A63B 69/00 | (2006.01) |
| A63B 69/18 | (2006.01) |
| A63B 69/36 | (2006.01) |
| A63B 69/38 | (2006.01) |
| A63B 21/055 | (2006.01) |
| A63B 21/068 | (2006.01) |
| A63B 71/06 | (2006.01) |
| A63B 21/005 | (2006.01) |
| A63B 21/00 | (2006.01) |
| A63B 22/00 | (2006.01) |
| A61H 7/00 | (2006.01) |
| A61N 1/36 | (2006.01) |
| A61N 1/04 | (2006.01) |

(52) U.S. Cl.
CPC ...... *A61F 2007/0045* (2013.01); *A61H 7/001* (2013.01); *A61H 2201/0207* (2013.01); *A61H 2201/0214* (2013.01); *A61H 2201/10* (2013.01); *A61H 2201/1284* (2013.01); *A61H 2201/164* (2013.01); *A61H 2201/168* (2013.01); *A61H 2205/125* (2013.01); *A61N 1/0452* (2013.01); *A61N 1/0472* (2013.01); *A61N 1/36003* (2013.01); *A63B 21/005* (2013.01); *A63B 21/0552* (2013.01); *A63B 21/068* (2013.01); *A63B 21/4034* (2015.10); *A63B 69/0002* (2013.01); *A63B 69/18* (2013.01); *A63B 69/36* (2013.01); *A63B 69/38* (2013.01); *A63B 2022/0038* (2013.01); *A63B 2071/0625* (2013.01); *A63B 2208/0204* (2013.01); *A63B 2213/00* (2013.01); *A63B 2213/004* (2013.01); *A63B 2220/17* (2013.01); *A63B 2220/20* (2013.01); *A63B 2220/52* (2013.01); *A63B 2225/09* (2013.01); *A63B 2225/50* (2013.01); *A63B 2225/64* (2013.01); *A63B 2225/66* (2013.01); *A63B 2230/04* (2013.01); *A63B 2230/40* (2013.01); *A63B 2230/50* (2013.01); *A63B 2230/75* (2013.01)

(58) Field of Classification Search
CPC .............. A61H 2205/125; A61H 7/001; A61H 2201/164; A61H 2201/1284; A61N 1/36003; A61N 1/0452; A61N 1/0472; A63B 26/003; A63B 22/14; A63B 22/16; A63B 2022/0038; A63B 21/005; A63B 2230/04; A63B 21/4034; A63B 2230/75; A63B 2230/50; A63B 2230/40; A63B 2225/66; A63B 2225/64; A63B 2225/50; A63B 2220/52; A63B 2220/20; A63B 2220/17; A63B 2213/004; A63B 2208/0204; A63B 2071/0625; A63B 69/0002; A63B 21/068; A63B 21/0552; A63B 69/38; A63B 69/36; A63B 69/18; A63B 2225/09; A63B 2213/00
See application file for complete search history.

(56) References Cited

U.S. PATENT DOCUMENTS

| | | | |
|---|---|---|---|
| 5,078,389 A * | 1/1992 | Chen | A63B 21/154 |
| | | | 482/147 |
| 5,433,683 A | 7/1995 | Stevens | |
| 5,830,107 A * | 11/1998 | Brigliadoro | A63B 23/03575 |
| | | | 482/1 |
| 6,162,150 A | 12/2000 | Lee | |
| 6,790,166 B2 | 9/2004 | Broudy | |
| 7,621,861 B1 * | 11/2009 | Kalember | A63B 22/14 |
| | | | 482/146 |
| 2002/0137610 A1 * | 9/2002 | Broudy | A63B 22/14 |
| | | | 482/147 |
| 2002/0151417 A1 * | 10/2002 | List | A63B 21/0552 |
| | | | 482/123 |
| 2007/0027009 A1 * | 2/2007 | Arnold | A63B 21/005 |
| | | | 482/146 |
| 2010/0010397 A1 | 1/2010 | Ochi | |
| 2010/0273619 A1 | 10/2010 | Ozawa | |
| 2011/0111927 A1 | 5/2011 | Kim | |
| 2011/0143896 A1 * | 6/2011 | Senegal | A63B 22/18 |
| | | | 482/139 |
| 2013/0331907 A1 | 12/2013 | Sumners et al. | |
| 2015/0209612 A1 * | 7/2015 | Shen | A63B 21/068 |
| | | | 482/147 |

* cited by examiner

COMBINATION THERAPEUTIC AND EXERCISE SYSTEM

CROSS-REFERENCE TO RELATED APPLICATIONS

The present application claims priority to U.S. Provisional Patent Application Ser. No. 62/111,110, entitled ROCKING 8BOARD AND VARIANTS, filed Feb. 3, 2015, all of the teachings of which are incorporated herein by reference.

STATEMENT RE: FEDERALLY SPONSORED RESEARCH/DEVELOPMENT

Not Applicable

BACKGROUND

Numerous exercise devices have been developed to promote a wide range of physical conditioning and enhance the ability of an individual to play a particular sport or perform a specific sports-type motion. With respect to the latter, it is well-known that proper form, coupled with appropriate balance and coordination, is crucial for sports such as golfing, tennis, bowling, pitching baseball/softball, and the like. Developing strength and conditioning, along with improved balance and coordination, is also extremely important when incorporated as part of a physical rehabilitation regimen where it is often crucial to develop muscle strength and range of motion so as to regain health and mobility.

Among the devices that have proven to be exceptionally effective in developing balance and coordination, along with strength and conditioning, include certain training apparatuses and methods of using such apparatuses as disclosed in U.S. Pat. No. 6,790,166B2 issued Sep. 14, 2004 to Broudy entitled BALANCE AND COORDINATION TEACHING METHOD, the teachings of which are expressly incorporated herein by reference. The apparatus disclosed in such reference, as well as the methods of using such apparatus, are exceptionally effective in developing balance and coordination via the use of first and second rotating platform members mounted on a planar base, each platform member being operative to receive the foot of a user. Each foot of the user is operative to rotate independently about a separate axis and can be utilized to properly perform certain motions that are crucial to properly performing any of a variety of sports, and in particular golf, tennis, skiing, surfing, martial arts and baseball, among others. The commercial embodiment of the apparatus and the use of such apparatus are sold under the trademark 8BOARD®, and marketed and distributed by Grail Sports, Inc. of Carlsbad, Calif.

Despite the exceptionally effectiveness of such apparatus, and the methods of using such apparatus to facilitate development of balance and coordination, and physical conditioning, such apparatus and the use of such apparatus have certain limitations. Specifically, the apparatus and the methods of using such apparatus typically require that the apparatus remain in stationary position on level ground. While such placement is optimal for performing certain motions specific to several sports, such as serving a tennis ball or swinging a golf club, the use of such apparatus is limited by the fact that the rotating platforms are maintained in generally parallel relation to the ground or other flat surface and the rotational movement of each respective platform extends about a perpendicularly extending axis. There is thus no ability for the user to experience dynamic or non-level orientations as would be encountered if, for example, the rotating platform surfaces were positioned on an incline or a surface operative to rock back and forth. Such added dimensions would be operative to provide additional challenges to the user, particularly with respect to balance and coordination, and would further enhance the ability of such apparatus to be used in training for skiing, surfing, or skateboarding, or any of a variety of dynamic activities that involve slopes, inclined surfaces, jostling motions and the like.

There are likewise numerous shortcomings associated with the apparatus and training methods of U.S. Pat. No. 6,790,166B2 due to the inability of such devices to impart any type of therapeutic effect to a user of such devices. While rehabilitation is among the many uses associated with such apparatus, such apparatus was originally designed to be utilized while the user is wearing shoes or other foot coverings, and thus incapable of imparting a therapeutic modality to the feet of a user, such as heat or cold, or provide a texturized surface that can be applied to the feet in order to provide a massaging effect. Such enhanced functionality has not heretofore been available with respect to the current use of the subject apparatus having rotational platforms and hence have limited functionality.

Indeed, the functionality of the subject apparatus could otherwise have benefited greatly due to a variety of modalities currently in use, such as a calorie counter, heart rate monitor, timer, sound/lighting/motivational modalities, monitors for measuring distance, respiration, and the like, and the ability to interface with computers or other portable electronic devices, which are currently in use and readily available to those skilled in the art. Along those lines, it is contemplated that the rotational platforms could benefit greatly by being individually manipulated so as to increase resistance and/or limit the range of rotational motion, so as to impart a selective range of motion or strengthening, as may be desired. Currently, there is a substantial need in the art for such enhancements that could be incorporated with such exercise apparatus and methods of using the same.

BRIEF SUMMARY

The present invention specifically addresses and alleviates the above-identified deficiencies in the art. In this regard, the present invention is directed to numerous substantial improvements that are integrated with the training apparatus as disclosed in U.S. Pat. No. 6,790,166B2, to Broudy, entitled "BALANCE AND COORDINATION TEACHING METHOD," issued Sep. 14, 2004, that enable the apparatus as disclosed therein to be used to provide further endurance training, conditioning, balance and coordination, as well as include numerous functionalities to promote exercise and impart any of a variety of therapeutic effects.

In a first series of embodiments directed to promoting balance and coordination, the invention incorporates the training apparatus of U.S. Pat. No. 6,790,166B2, whereby the stationary base member having first and second rotating platforms mounted thereon are further positionable upon a specialized mount. The specialized mount may take any of a variety of shapes and sizes, and are operative to position the base member with rotating platforms mounted thereon in a specific orientation or facilitate the ability of the base member and rotating platforms to further move about in a particular motion. In one embodiment, the specialized mount comprises a semi-cylinder defining an upper surface for receiving the base member with rotating platforms mounted thereon. To facilitate the ability of the base member to interconnect with the upper platform surface of the semi-cylinder, it is contemplated that mounting apparatus disposed on the platform surface will be operative to interconnect with the base member. In one preferred embodiment, mounting members comprise one or more anchor portions extending upwardly from the semi-cylinder platform surface operative to interconnect with apertures formed upon the base member.

Once the base member with rotating platforms is mounted upon the platform surface of the semi-cylinder, the user may stand upon such apparatus and perform clockwise and counter-clockwise rocking motions while each respective foot of the user is operative to rotate independently upon each respective rotating platform. Not only does the base member with rotating platform members facilitate balance and coordination, the further rocking motion afforded by the semi-cylinder specialized mount provides a further challenge to the user to thus further enhance balance and coordination.

In an alternative embodiment, the specialized mount is formed to define an upwardly-extending incline upon which the base member with rotating platform members may be positioned. Instead of each rotating platform being maintained in substantially parallel relation to the ground or other flat surface, with the rotating motion being provided along an axis extending perpendicular to the ground or flat surface, the specialized mount is positioned such that the base member and each rotating platform rotates about an angled axis that provides a further challenge to the user in terms of maintaining balance and coordination in an off-set orientation as the user stands upon the device and performs rotational movements upon each respective rotating platform members.

To enhance the ability of the rotating platform members to be selectively positioned maintained in fixed position relative one another when in use, the present invention further contemplates that the base member upon which the rotating platforms are mounted may be designed to have a split configuration whereby the base member is defined by first and second sections that can selectively interconnect with one another to increase or decrease the width of the base, so a greater degree of distance of the rotating platform members are maintained apart from one another. In a preferred embodiment, the base member is comprised of a plurality of apertures formed in a grid-type system that not only facilitates the ability of the user to selectively position the rotating platform members on the base member, but also facilitates the ability of the base member to be selectively interconnected to a specialized mount. In a highly preferred embodiment, the base member will have a honeycomb-like arrangement of hexagonal apertures wherein each aperture is operative to receive and interconnect with male-type hexagonal members to thus define an interlocking fit. In this regard, such base member may take the form of those base members disclosed in Applicants' related U.S. patent application Ser. No. 14/858,728, entitled MODULAR STORAGE SYSTEM AND WORK STATION, filed Sep. 18, 2015, and Ser. No. 14/858,797, entitled SPLIT ROTATING KEYBOARD SYSTEM, filed Sep. 18, 2015, the teachings of which are expressly incorporated herein by reference.

In addition to the enhanced structure and ability to be utilized with specialized mounts that can be used in training and for providing yet a greater degree of balance and coordination conditioning, the present invention further contemplates including a number of functionalities that enhance operation of the device, as well as can impart any of a variety of therapeutic effects. With respect to the former, it is contemplated that the rotating platforms incorporated as part of the system can be provided with selective resistance to thus make it more challenging for the user to perform rotational movements on such platform surfaces to thus improve strength. Also, the range of rotational movement of each respective platform may be selectively adjusted so as to limit the range of motion that an individual can rotate such platform. It is likewise contemplated that any of a variety of electronic functionalities may be included as part of the device, including a calorie counter to count the calories an individual expends performing activities on each rotating platform, the distance swiveled, duration of exercise, types of rotational activities performed, and the like can be monitored, stored in a data base or fed into a display for analysis and assessment by the user. Other types of functionalities can include incorporating sound generating devices such as beeps, music, motivational recordings and the like configured to execute upon certain rotational movements performed on the rotating platforms. Other examples include integrating a timer, heart monitor, rotation counter, sensors attachable to the user to measure respiration or the ability of the device to integrate with other applications and the like. These additional biometric measuring capabilities can be implemented on the invention itself, or be on a receiving device such as a phone, tablet, or watch which interprets signals from the sensors on the invention which are transmitted to the receiving device wirelessly. The controlling device may even alert or entertain the user based on the detected movements.

With respect to imparting a therapeutic event, it is further contemplated that the rotating platforms may further be operative to impart a therapeutic temperature to the feet of a user, such as heat or cold, as may be desired for a particular application. It is further contemplated that the rotating platforms may be provided with a texturized surface, that either independently or in combination with the delivery of hot or cold temperatures, may provide a massaging effect to the user's feet. In this regard, simply standing on the rotating members and performing even modest rotational movements can impart a highly beneficial therapeutic effect. The rotating platforms may also include electrodes which transmit specifically designed electrical stimulation to the user's feet. Such electrical stimulation can even be turned on or off by a controlling device such as a phone, tablet, or watch. The same controlling device may also allow the user to choose the types of stimulation, intensity, duration, and the like.

BRIEF DESCRIPTION OF THE DRAWINGS

These, as well as other features of the present invention, will become more apparent upon reference to the drawings wherein.

DETAILED DESCRIPTION

The detailed description set forth below is intended as a description of the presently preferred embodiment of the invention, and is not intended to represent the only form in which the present invention may be implemented or performed. The description sets forth the functions and sequences of steps for practicing the invention. It is to be understood, however, that the same or equivalent functions and sequences may be accomplished by different embodiments and that they are also intended to be encompassed within the scope of the invention.

Figure 1:
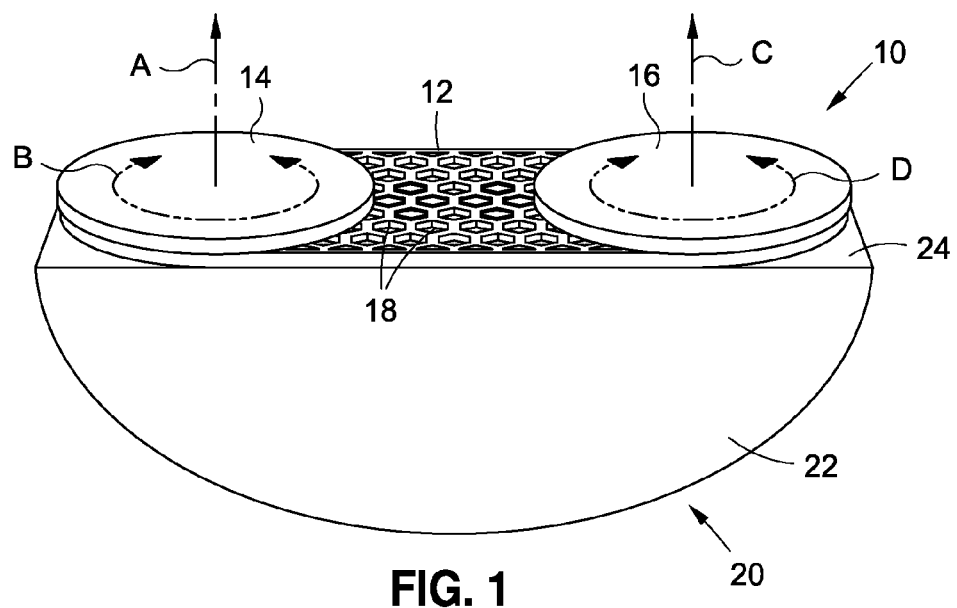
FIG. 1 is a perspective view of a training apparatus including a base member and first and second rotating platforms mounted thereon, the base and rotating platforms further being positioned upon a specialized mount.

Referring now to the figures, there is shown a combination therapeutic and exercise system as constructed in accordance with several embodiments of the present invention. Starting with FIG. 1, the system comprises a first training apparatus portion 10 in combination with a specialized mount 20. With respect to the former, the training apparatus 10 comprises the combination of a central base portion 12 upon which are disposed rotating platform members 14,16. As illustrated, rotating platform 14 is operative to rotate about axis A in the clockwise and counter-clockwise directions indicated by the letter B. Similarly, second rotating platform 16 is operative to rotate about axis C such that the platform 16 can rotate in the clockwise and counter-clockwise directions indicated by the letter D. In the embodiments shown, axes A and C are generally parallel to one another. The structure and configuration of the training apparatus 10 preferably takes the form of those disclosed in U.S. Pat. No. 6,790,166B2, entitled BALANCE AND COORDINATION TEACHING METHOD issued Sep. 14, 2004, the teachings of which are expressly incorporated herein by reference. The present invention utilizes such structure but enhances such structure in the manner discussed herein which enables those devices and methods disclosed in U.S. Pat. No. 6,790,166 to be substantially enhanced in terms of functionality and effectiveness.

To that end, base member 12 is preferably provided with a plurality of a apertures 18 that facilitate the ability of base member 12 to remain interconnected to a number different items, such as specialized mount 20. Apertures 18 formed upon base member 12 are further operative to provide means for interconnecting with the rotating platforms 14,16 to thus enable the rotating platforms 14,16 to be selectively positioned on such base member 12.

Figure 2:
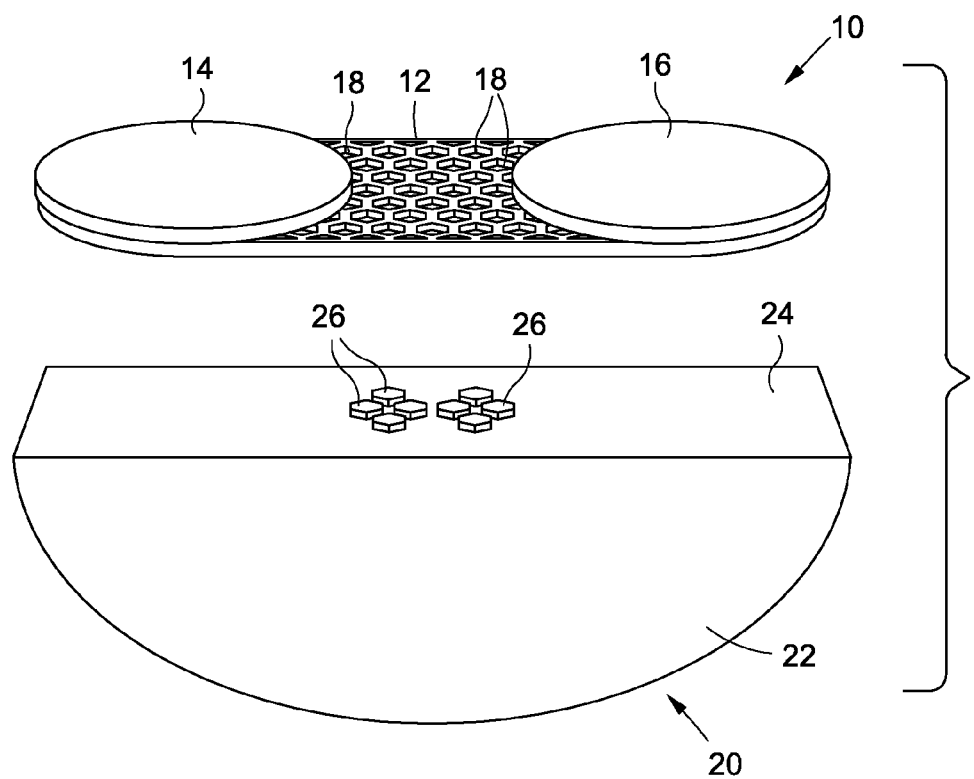
FIG. 2 is an exploded view of the base member with rotating platforms mounted thereon, as shown in an orientation to be fitted upon specialized mount of FIG. 1. Although not shown, the two rotating platforms can also be detached from the base member.

Along those lines, and referring to FIG. 2, the training apparatus 10 is operative to become detachably mounted upon and interconnected with specialized mount 20 in the exploded view shown. The apertures 18 formed about base member 12 are operative to align with and receive anchor members 26 formed upon platform surface 24 of specialized mount 20. In the configuration shown, the specialized mount 20 is formed as a semi-cylinder 22 which thus provides the curved contours resembling a semi-circle and defining the platform surface 24 as shown. Thanks to the use of standardized fitting elements, training apparatus 10 does not have to be evenly aligned with the specialized mount 20. The user can mount the training apparatus 10 off the center (slightly to the right or the left) if there is a reason to do so (e.g., for the purpose of stressing one leg more than the other).

Figure 3:
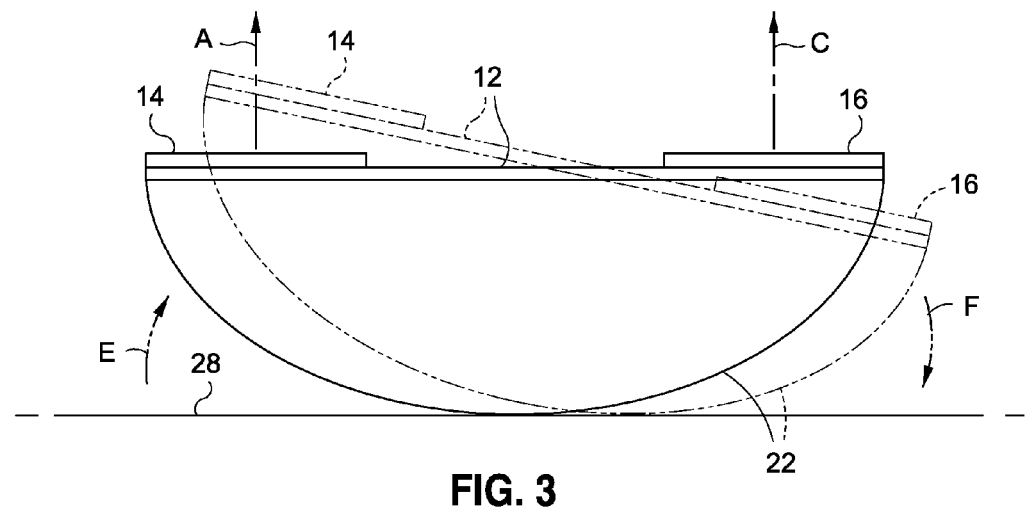
FIG. 3 is a side view of the base member with rotating platforms as mounted upon specialized mount shown in a first stationary position, and a second clockwise rocking position shown in phantom.
Figure 4:
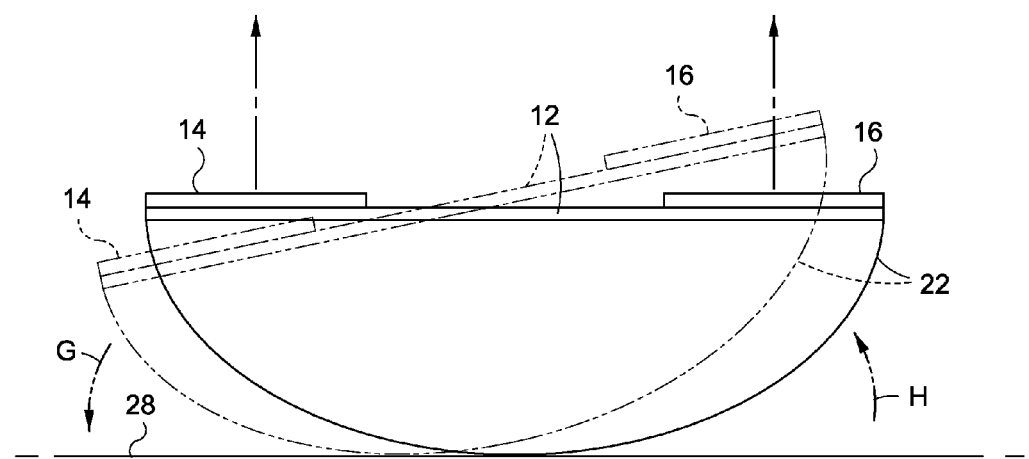
FIG. 4 is the side view of FIG. 3 showing the base member with rotating platforms as mounted upon specialized mount shown in a first stationary position and in a second counter-clockwise rocking motion shown in phantom.

Referring now to FIGS. 3 and 4, when base portion 12 is secured to the upper platform surface 24 of semi-cylinder 22, a user, standing upon the training apparatus 10 such that one foot of the user is on rotating platform 14, and the respective other foot is on rotating platform 16, can use the device such that movement of each foot can rotate about the central axes A,C per the teachings of U.S. Pat. No. 6,790,166. By positioning the base member on the specialized mount having the semi-cylindrical shape 22 as shown, the base member 12 with rotating platforms 14,16 mounted thereon is operative to rock in both clockwise and counter-clockwise rotational motions. In this regard, semi-cylindrical mount 22 can rock in a clockwise manner indicated by the directions E and F shown in FIG. 3, as well as counter-clockwise rocking motions indicated by the letters G and H shown in FIG. 4. As such, the user standing upon the rotating platform 14,16 are not only operative to move their feet about rotating axes A,C, but are able to do so while the rotating platforms 14,16 move in a rocking fashion by virtue of their connection with base 12 and upper platform surface 24 of semi-cylindrical mount 22.

As a consequence, the user is thus able to be substantially more challenged by having to maintain coordination and balance while not only performing rotating motions on each respective rotating platform members 14,16, but also to do so while the plane on which the rotating platforms 14,16 are positioned continuously rocks in clockwise and counter-clockwise motions as shown. The user is thus forced to demonstrate substantially more coordination and balance, which in turn promotes further strengthening and muscle training. Such motions are exceptionally effective when training for fluid-type sports that require extreme agility and the ability to be balanced and coordinated when encountering uneven or sloping surfaces and/or jostling-type forces, as are typically encountered in sports such as skiing, surfing, skateboarding and the like.

As will be appreciated by those skilled in the art, the specialized mounts 20 such as the semi-cylindrical member 22 with platform surface 24 as shown, may take any of variety of shapes and sizes, and may have specific dimension operative to impart a specific type of movement or motion, such as the rocking motions depicted in FIGS. 3 and 4. Such specialized mount 20 may also be fabricated from any of a variety of materials, such as plastics, wood, metal or any other suitable material operative to form the desired shape, as well as to support the training apparatus 10 in the manner illustrated. Specialized mount 20 may also be fabricated from a deformable rubber type material so as to flex, compress, expand and the like to impart a further dynamic effect.

Figure 5:
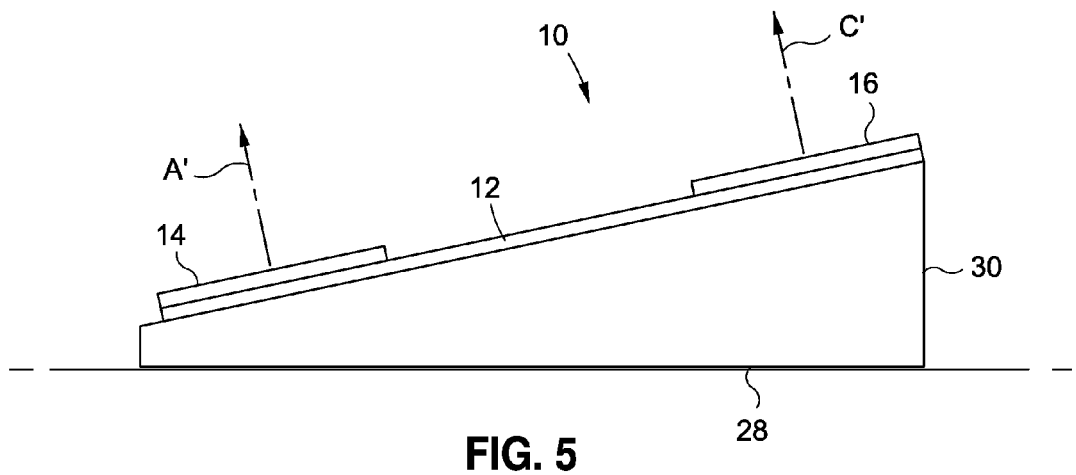
FIG. 5 is an alternative embodiment of the present invention where the specialized mount is a stationary incline mount operative to maintain the base member with rotating platforms mounted thereon in an angled configuration.
Figure 6:
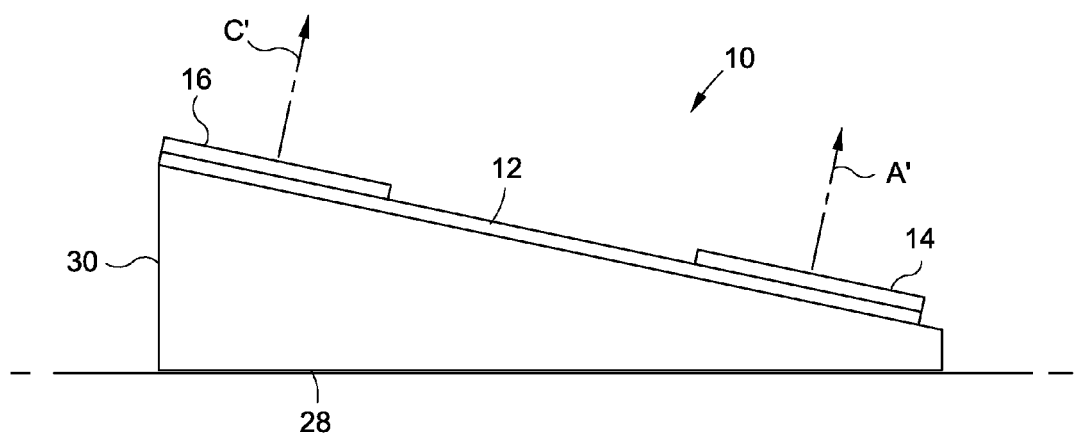
FIG. 6 is the opposite side view of a specialized mount with base member with rotating platforms mounted thereon shown in FIG. 5.

Referring now to FIGS. 5 and 6, and initially to FIG. 5, there is shown the training apparatus 10 comprised of base member 12 and rotating platform members 14,16 mounted thereon, as supported upon specialized mount 30, the latter having an incline relative the level surface 28 upon which the specialized mount 30 is positioned. As illustrated, the base member 12, by virtue of being interconnected upon the top surface of specialized mount 30, is operative to extend in an upwardly ascending incline, as shown in FIG. 5, and a descending incline, shown in FIG. 6 when viewed from left to right. While in such configuration, the rotating platform members 14,16 are operative to rotate about tilted axes A'C'. By providing rotating platforms 14,16 that rotate about axes A'C' that are not perpendicular with ground 28, the user is thus challenged to provide rotational movements upon such rotating platforms 14,16 per the challenge introduced by the inclining slope provided by the upper surface of specialized mount 30. Such stationary incline configuration is operative to promote coordination and balance, as well as strength training, as the body performs rotational movements that must further take into effect gravity and the ability to remain on the rotating platforms 14,16 while the user stands in such incline configuration. By positioning the apparatus 20 in the manner shown, the user is thus able to practice rotational movements that are typically encountered in sports such as skateboarding, surfing and skiing, as discussed above.

Figure 7:
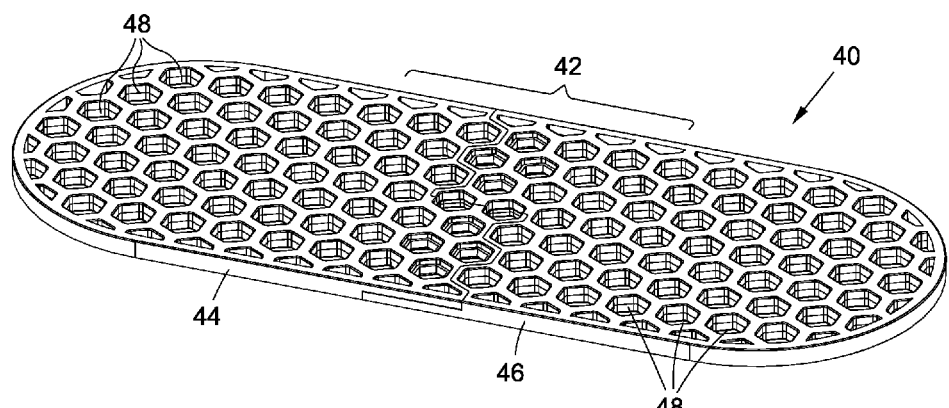
FIG. 7 is a perspective view of a base member upon which the first and second rotating platforms may be mounted, the base member being constructed in accordance with a preferred embodiment and operative to be selectively adjustable.

Referring now to FIGS. 7-10, initially to FIG. 7, there is shown a base platform system 40 as constructed in accordance with a preferred embodiment of the present invention as operative to serve as the stationary base member 12 as discussed in the earlier figures. While it is expressly contemplated that the stationary base 12 may take any of a variety of forms well-known to those skilled in the art, and as discussed above may be provided with a plurality of apertures formed in a grid-like fashion, the base portion system 40 as shown serves numerous advantages that have not heretofore been available. As illustrated, the system 40 defines an upper platform surface 42 consisting of a plurality of apertures 48 into which complementary male-type anchor members may be inserted and fit into position. As discussed earlier, the apertures are operative to receive anchor members such as 26 formed on platform surface 24, and may also be configured to receive and mount with like anchor devices formed on the underside portions of rotating platform members 14,16 (not shown). The apertures 48 may further be preferably formed as hexagons and formed in a honeycomb-like configuration as disclosed in Applicants' co-pending U.S. patent application Ser. No. 14/858,728, entitled MODULAR STORAGE SYSTEM AND WORK STATION, filed Sep. 18, 2015, and Ser. No. 14/858,797, entitled SPLIT ROTATING KEYBOARD SYSTEM, filed Sep. 18, 2015, the teachings of which are expressly incorporated herein by reference.

Figure 8:
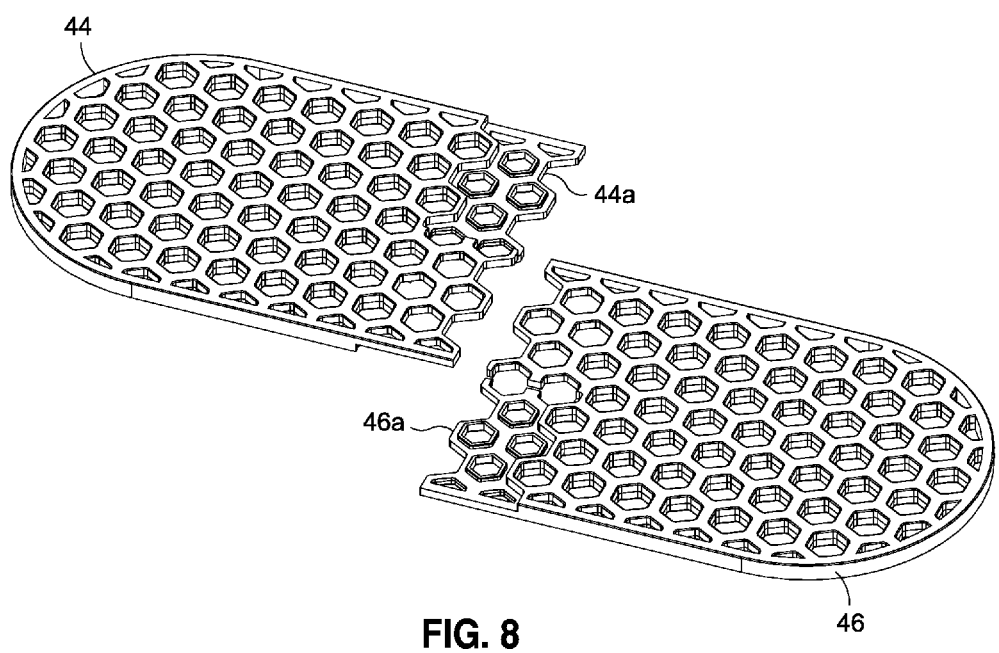
FIG. 8 is a perspective view of the base member of FIG. 7 shown in detached first and second sections.
Figure 9:
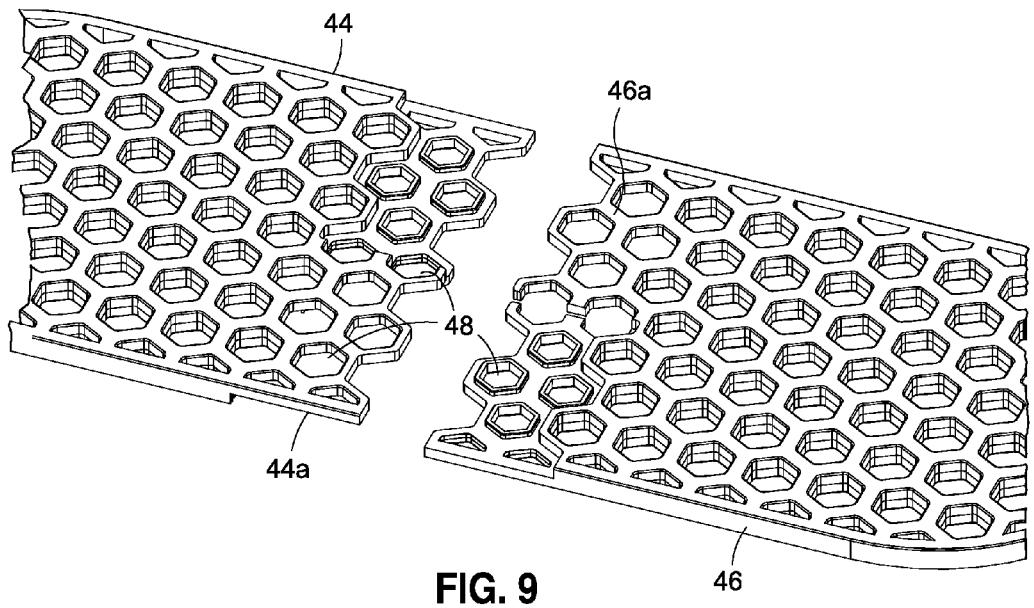
FIG. 9 is a view of the midpoint of the first and second sections depicted in FIG. 8 showing how such first and second sections are operative to interconnect with one another to form the structure of FIG. 7.
Figure 10:
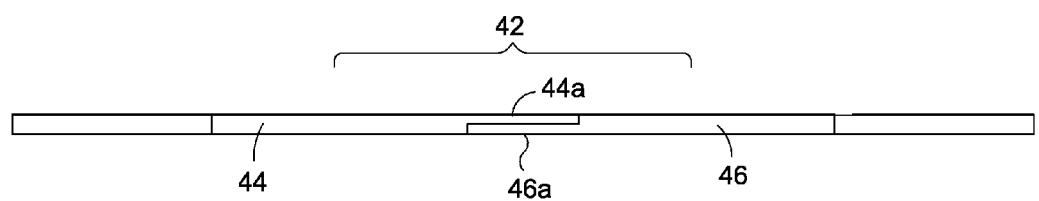
FIG. 10 is a side-view of the base member depicted in FIG. 7 showing the first and second sections interconnected to one another.

The system 40 as shown, in order to provide greater versatility, is preferably divided into a first section 44 and a second section 46 that are detachably interconnectable to one another, as more clearly shown in FIG. 8. In this regard, first portion 44 is provided with an overhang portion 44a that detachably mates with extended under-portion 46a of second section 46. As shown in FIG. 9, the portions 44a,46a are complementary in nature and can be selectively reattached to produce a wider upper surface 42 as may be desired. In the embodiment shown, the width of the upper surface 42 may be adjusted by one to two rows apertures 48 while still enabling the first and second sections 44,46 to mate with and become attached with anchor members disposed there-underneath or there-over along interconnecting portions 44a,46a, as will be understood by those skilled in the art. To the extent it is not desired to expand the width of upper surface 42, the first and second sections 44,46, may be interconnected with one another in the manner shown in FIG. 10 such that portions 44a,46a are completely attached to one another. Furthermore, there can be an additional intermediate "extender" which consists of mating surfaces of 44a and 46a on both sides of the element and can lengthen the base member indefinitely.

Figure 11:
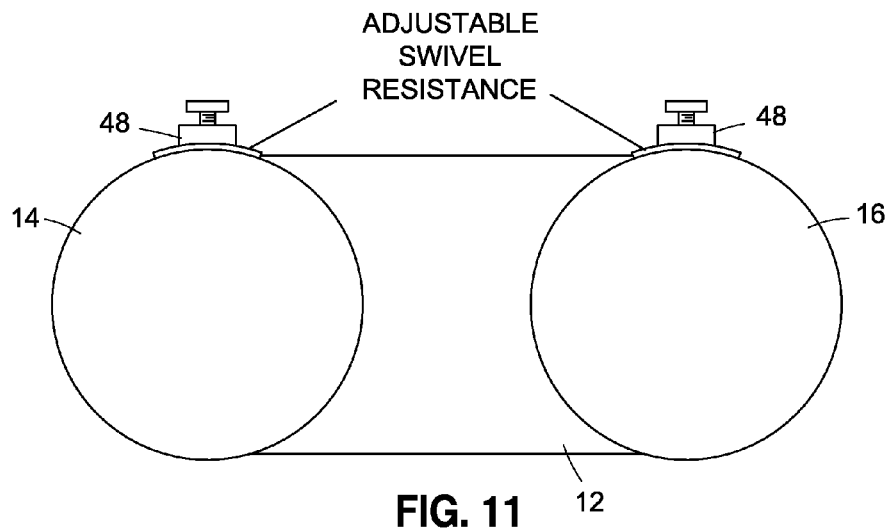
FIG. 11 is a top view of the base member with rotating platforms mounted thereon shown having an adjustable swivel resistance.

In addition to providing enhanced functionality in terms of more challenging environments to test balance and coordination, the present invention further contemplates that the training apparatus, and more particularly the rotating platform members 14,16 thereof, can be adapted to provide numerous enhanced functionalities and therapeutic modalities. With respect to the former, and referring to FIG. 11, it is contemplated that the rotating platforms 14,16 may be designed to have a selectively adjustable swivel resistance, such that the rotational movement on each respective platform 14,16 may be controlled so as to increase difficulty, and hence increase muscle training, to the extent the user's feet make rotational movements thereon. It is further contemplated that such resistance can be set such that the rotational movement of each respective platform member 14,16 is limited in nature, such that less than complete 306° rotation is selectively implemented. Such resistance and limitations on rotational movement may be accomplished by any of a variety of electromechanical mechanisms well-known to those skilled in the art, including but not limited to simple resistance knobs 48 as shown as attached to respective ones of the rotating platform members 14,16. Resistance can also be provided by electromagnets or elastic bands placed at appropriate positions.

In addition to modifications such as resistance and limiting the rotational movement of platform members 14,16, it is further contemplated that any of a variety of well-known exercise technologies and applications may be readily integrated with the training apparatus 10 as part of the systems of the present invention. In this regard, it is contemplated that any of a variety of electronic devices can be attached to and integrated with the training apparatus, for example sensors may be integrated as part of the rotating platform members 14,16. The apparatus may also be that are operative to measure speed of rotation, degree of rotation, make calculations such as counting calories, perform timing functions, count repetitions, measure weight/balance distribution over the rotating platform members 14,16. The apparatus may also be integrated with any of a variety of accessories that can produce lighting upon certain degrees of rotation, produce sound such as beats, music, motivational messages and the like, as well as integrate with other exercise applications utilized with cell phones, computers, tablets, watches and other types of portable electronic devices. In one preferred implementation, sensors on the invention transmit basic movement and positional signals to a receiving device such as a phone, tablet, or a watch, and the receiving device does the interpretation and calculations and displays the desired data to the user, or entertains the user with any variety of audiovisual output based on data from the sensors.

It is further expressly contemplated that the rotating platform members 14,16 may be interconnected to one another such that rotational movement on one platform is caused to stop while the respective other is allowed to swivel. It is likewise contemplated that the rotational resistance of the rotating platforms 14,16, as discussed above, may not only be selectively adjusted, but selectively increased or decreased over time as may be desired for resistance training or for rehabilitation and strength training.

It is likewise contemplated that any of a variety of sensors attachable to a user's body and operative to measure physiological conditions, such as respiratory rate, breathing patterns, body temperature, range of motion, or any of a variety of physiological parameters that can be measured, may be integrated in combination with a user's use of the systems of the present invention. Along those lines, it is contemplated that the use of the systems of the present invention can be integrated with computer modeling other video-type technologies that are operative to provide assessment and training of a user's motions, as may be incorporated as part of a sports training regimen, particularly with respect to the analysis and performance of sports motions, such as the swinging of a golf club, tennis racket, baseball bat, and the like. Accordingly, all such limitations and functionalities as presently known or developed in the future are deemed to fall within the scope of the present invention.

Figure 12:
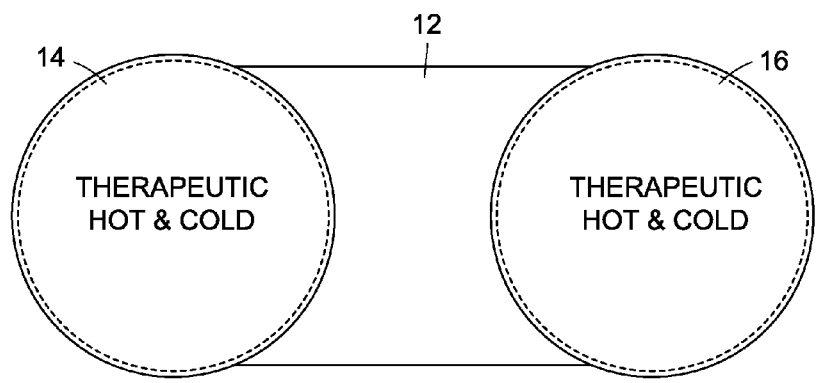
FIG. 12 is a top view of the base member with rotating platforms mounted thereon operative to impart a therapeutic temperature to the feet of a user, namely hot or cold temperatures.
Figure 13:
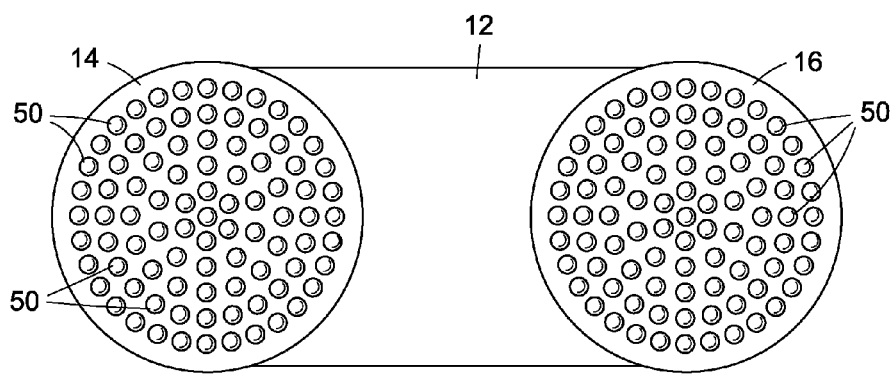
FIG. 13 is a top view of the base member with rotating platforms formed thereon with the upper surface of the rotating members having a texturized upper surface for imparting a therapeutic massage effect to the feet of a user.

Referring now to FIGS. 12 and 13, and initially to FIG. 12, there is further shown how the systems of the present invention may be operative to impart a desired therapeutic effect to the feet of a user. As illustrated, rotating platforms 14,16 may further be operative to impart a therapeutic temperature directly to the feet of the user, which may be either heat or cold as may be desired for a particular application. As is well-known to those skilled in the art, the application of either hot or cold temperatures, particularly with respect to the feet of the user, may impart a desired therapeutic effect. It is contemplated that any of a variety of heat transferring devices or cooler-type device known in the art may be readily integrated as part of the top platform surface of the rotating platform members 14,16 so as to impart the desired heated or refrigerated effect.

Similarly, with respect to FIG. 13, the upper platform surfaces of rotating platforms 14,16 may be provided with a texturized surface, such as formed with a plurality of protuberances 50 as shown, that are operative to provide a massaging therapeutic effect to the user's feet when positioned thereon. Along those lines, it is contemplated that the texturized surface, such as the protuberances 50 shown in FIG. 13, may be combined with the therapeutic hot and cold temperature devices integrated as part of FIG. 12 to thus provide a multi-therapeutic effect whereby desired temperature is applied to the user's feet while also providing a massaging-type sensation. Any of a variety of other therapeutic modalities are also contemplated as being within the scope of the present invention as would be easily understood by those skilled in the art.

Similarly, with respect to FIG. 13, the upper platform surfaces of rotating platforms 14,16 may also include electrodes that transmit specifically designed electrical stimulation to the user's feet. Such electrical stimulation can even be turned on or off by a controlling device such as a phone, tablet, or watch. The same controlling device may also allow the user to choose the types of stimulation, intensity, duration, patterns etc. Such stimulation may be of either therapeutic or entertainment purposes.

Additional modifications and improvements of the present invention may also be apparent to those of ordinary skill in the art. Thus, the particular combination of parts and steps described and illustrated herein is intended to represent only certain embodiments of the present invention, and is not intended to serve as limitations of alternative devices and methods within the spirit and scope of the invention.

What is claimed is:

1. A combination therapeutic and exercise system, the system comprising:
 a base member positionable on a planar surface;
 a first platform member positioned upon the base member, the first platform member having a platform surface being formed to rotate about a first axis and operative to receive and support a respective one of a user's feet;
 a second platform member positioned upon the base member, the second platform member having a platform surface being formed to rotate about a second axis and operative to receive and support a respective one of the user's feet extending along a continuous plane relative said first platform surface; and
 an electronic device or sensors integrated with said first and second rotating platform members and operative to generate data corresponding to the user's activities when rotating the user's feet upon said first and second rotating members, said data being selected from the group consisting of a number of calories the user expends while standing and performing rotational motions upon the first and second rotating platform members, an amount of time the user stands upon the first and second rotating members, the user's heart rate while using or standing on the first and second rotating platform members and a distance of rotational movement generated by the user while standing on the first and second rotating platform members;
 wherein said base member defines a plurality of apertures arranged in a grid, at least one of said apertures interconnects and anchors with male anchor members positionable in respective said at least one of said apertures.

2. The system of claim 1 wherein the system further comprises a therapeutic modality operative to impart a therapeutic effect to the feet of the user standing upon the first and second rotating platform members.

3. The system of claim 2 wherein the therapeutic modality is selected from the group consisting of imparting a heated temperature to each respective foot of said user, imparting a cooling temperature to each respective foot of the user, and imparting a massage effect to each respective foot of the user.

4. The system of claim 3 wherein the therapeutic modality is imparting the massaging effect to each respective foot of the user, and wherein said massaging effect is imparted by a plurality of protuberances formed on an upper rotating platform surfaces of each respective said first and second rotating platform member.

5. The system of claim 2 wherein the therapeutic modality is operative to provides electrical stimulation.

6. The system of claim 1 further comprising a specialized mount upon which said base member with said first and second rotating platform members mounted thereon are detachably securable.

7. The system of claim 6 wherein the specialized mount comprises a horizontal base portion positionable on level ground and an upper inclined surface, the upper inclined surface defining a platform for detachably receiving said base member with said first and second rotating platform members mounted thereon.

8. The system of claim 7 wherein said horizontal base portion is comprised of first and second sections that are detachably interconnectable with one another.

9. The system of claim 8 wherein said horizontal base portion has a width that is adjustable via selectively interconnecting said first and second sections to one another.

10. The system of claim 1 wherein said apertures comprise hexagonal-shaped apertures.

\* \* \* \* \*